United States Patent [19]
Kesling

[11] Patent Number: 5,873,716
[45] Date of Patent: Feb. 23, 1999

[54] ORTHODONTIC HOOK ASSEMBLY AND APPLIANCE

[75] Inventor: Christopher K. Kesling, LaPorte, Ind.

[73] Assignee: TP Orthodontics, Inc., LaPorte, Ind.

[21] Appl. No.: 852,046

[22] Filed: May 6, 1997

[51] Int. Cl.⁶ .................................................. A61C 3/00
[52] U.S. Cl. .................................. 433/22; 433/14; 433/18
[58] Field of Search ................................ 433/14, 18, 19, 433/17, 22, 24

[56] References Cited

U.S. PATENT DOCUMENTS

| | | | |
|---|---|---|---|
| D. 346,860 | 5/1994 | Kesling | D24/180 |
| 2,062,395 | 12/1936 | Brusse et al. | 433/23 |
| 3,052,027 | 9/1962 | Wallshein | 433/9 |
| 3,158,934 | 12/1964 | Waldman | 433/22 |
| 3,453,734 | 7/1969 | Rubin | 433/22 |
| 3,508,332 | 4/1970 | Armstrong | 433/21 |
| 3,657,817 | 4/1972 | Kesling | 433/14 |
| 3,690,003 | 9/1972 | Gerber | 433/18 |
| 3,793,730 | 2/1974 | Begg et al. | 433/14 |
| 3,893,241 | 7/1975 | Moriarty | 433/22 |
| 3,905,111 | 9/1975 | Kesling | 433/8 |
| 3,913,228 | 10/1975 | Wallshein | 433/18 |
| 3,985,282 | 10/1976 | Miller et al. | 228/175 |
| 4,083,113 | 4/1978 | Miller et al. | 433/17 |
| 4,230,104 | 10/1980 | Richter | 433/18 |
| 4,427,381 | 1/1984 | Hall | 433/14 |
| 4,478,577 | 10/1984 | Warren, Jr. | 433/14 |
| 4,595,361 | 6/1986 | Blechman et al. | 433/18 |
| 4,639,219 | 1/1987 | Gagin | 433/22 |
| 5,035,614 | 7/1991 | Greenfield | 433/21 |
| 5,057,012 | 10/1991 | Kesling | 433/17 |
| 5,125,832 | 6/1992 | Kesling | 433/8 |
| 5,154,606 | 10/1992 | Wildman | 433/8 |
| 5,161,969 | 11/1992 | Pospisil et al. | 433/8 |
| 5,205,736 | 4/1993 | Blechman | 433/18 |
| 5,232,364 | 8/1993 | Rosen | 433/173 |
| 5,306,142 | 4/1994 | Richards | 433/22 |
| 5,338,191 | 8/1994 | Hamula | 433/23 |
| 5,470,228 | 11/1995 | Franseen et al. | 433/8 |
| 5,529,491 | 6/1996 | Hilgenfeldt et al. | 433/23 |
| 5,540,586 | 7/1996 | Hanson | 433/22 |

OTHER PUBLICATIONS

TP Orthodontics, Inc. advertisement; "If we wanted a Crimpable Hook tomove we would have designed it that way"; no date.

Celebrating 50 years TP Orthodontics brochure; no date.

*Primary Examiner*—John J. Wilson
*Attorney, Agent, or Firm*—Barnes & Thornburg

[57] ABSTRACT

An orthodontic appliance includes brackets, an arch wire and a hook for receiving an elastic member. The hook is movable from a first position when the elastic is not positioned about the hook to a second position when the elastic member is positioned about the hook. In one embodiment, the orthodontic appliance includes a clamp pivotable about the arch wire, a tube connected to the clamp and to the hook, and a second wire connected to the tube and to at least one of the brackets. In another embodiment, magnets are secured to the arch wire. One of the magnets can pivot about the arch wire and includes a hook attached thereto. In another embodiment, an orthodontic appliance includes brackets, an arch wire, a clamp secured to the arch wire, a hook and a wire. The wire is secured to the clamp and the hook. The hook is movable in response to a force applied by an elastic member. In another embodiment, an orthodontic appliance includes brackets, an arch wire, a hook and a wire segment. The wire segment is connected to one of the brackets and the hook. The hook is movable in response to a force applied by an elastic member. One of the brackets includes a slot and the wire segment extends into the slot. In another embodiment, an orthodontic appliance includes brackets, a tube and an arch wire extending through the brackets and tube. A spring loaded hook is connected to the clamp by a hinge.

61 Claims, 11 Drawing Sheets

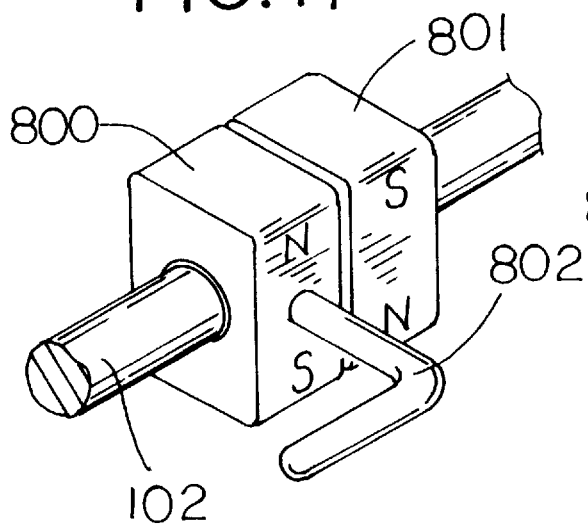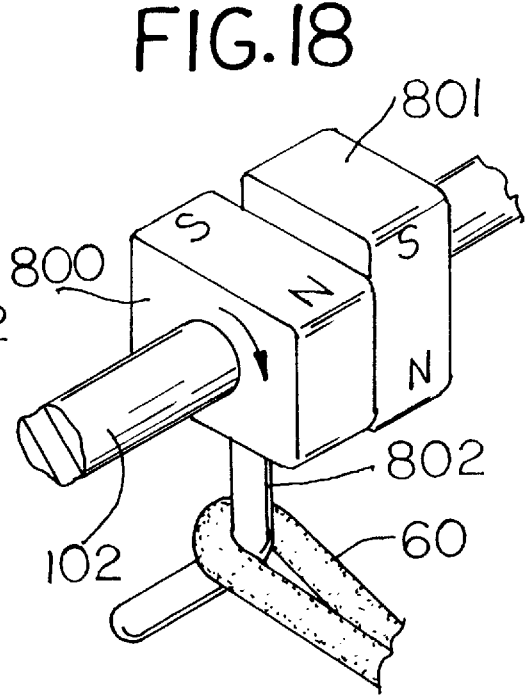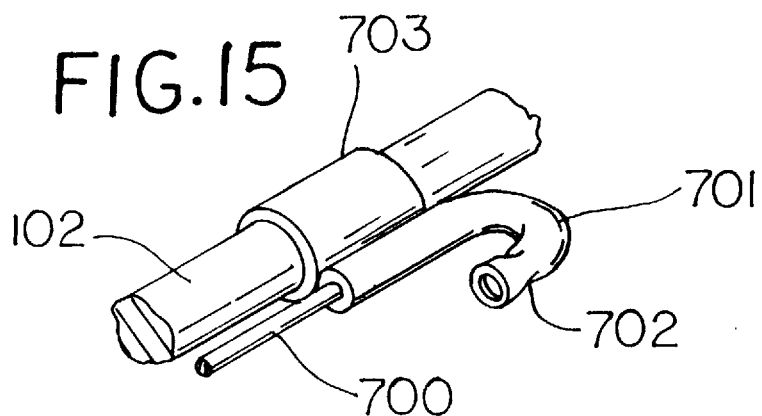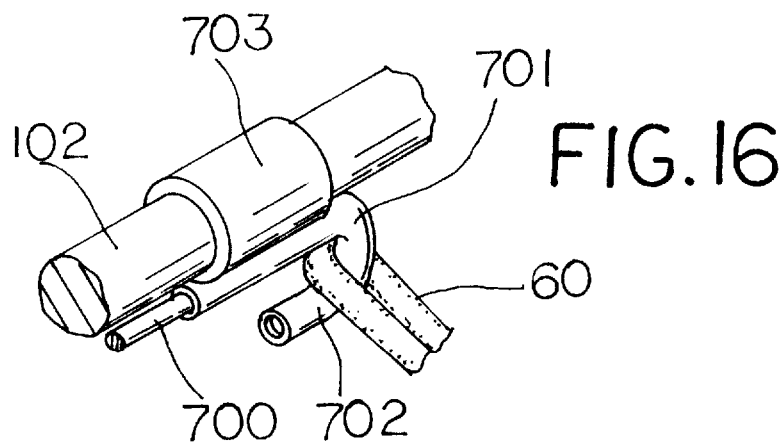

ORTHODONTIC HOOK ASSEMBLY AND APPLIANCE

BACKGROUND AND SUMMARY OF THE INVENTION

The present invention relates to orthodontic appliances and, in particular, to hooks for securing elastic members to orthodontic braces.

Orthodontic braces are well known. Typically, braces include one or more brackets secured to the teeth of the patient. The brackets may be secured in a number of ways. One manner of securing the brackets is to adhere them to the surface of the teeth with a suitable adhesive. Alternatively, the brackets may be secured to the teeth by attaching them to a series of bands that encircle the individual teeth. Once the brackets are secured to the teeth, it is typical to install what is known as an arch wire through the brackets. The arch wire may extend through slots in some or all of the brackets and be anchored at each end to a bracket secured to one of the patient's molars.

Often, elastic members in the form of small rubber bands are utilized to apply additional tension to the braces, which in turn transmit the tension to the teeth. Typically, a pair of hooks is provided for securing the elastic member to the braces. One hook is typically located on the lower set of braces and one on the upper set of braces. The elastic member is secured about one hook and then stretched and secured about the second hook so as to extend from the upper set of braces to the lower set of braces.

The elastics are usually applied by the patient and are periodically changed. For example, the elastics are typically removed when the patient brushes his or her teeth and new ones are put on. Sometimes, the elastics will break or become disengaged from the braces and fall out. In these instances, new elastics are again applied by the patient.

Orthodontists have found that patients do not always replace their elastics once they have been removed for a given reason. For example, it is not unusual for younger wearers of braces, such as teenagers, to fail to wear their elastics. Thus, the patient's treatment may be prolonged because the proper tension is not being applied to the braces in the absence of the elastics.

The present invention provides orthodontic hook assemblies that position the hooks such that they contact the interior of the patient's mouth and cause discomfort when the elastics are not applied to the hooks. When the elastics are applied, the hooks move to positions in which they do not contact the interior of the patient's mouth.

These and other features of the present invention are attained by an orthodontic appliance having a plurality of brackets, an arch wire connected to the brackets and hooks for receiving an elastic member. One or more of the hooks are movable from a first position when the elastic member is not positioned about the hook to a second position when the elastic member is positioned about the hook. The hook extends in the labial direction when the elastic member is not positioned about the hook and in the incisal direction when the elastic member is positioned about the hook.

According to one embodiment of the present invention, the orthodontic appliance further includes a clamp pivotable about the arch wire, a tube connected to the clamp and to the hook, and a second wire connected to the tube and to at least one of the brackets. The second wire may be a shape memory wire.

According to another embodiment of the present invention, the orthodontic appliance includes a clamp pivotable about the arch wire, a tube connected to the clamp and a second wire extending into the tube. The tube and second wire are bent to form the hook.

In another embodiment of the present invention, an orthodontic appliance further includes two magnets. The first is secured to the hook and the second is secured to the arch wire. The arch wire extends through the first magnet and the first magnet is pivotable about the arch wire.

According to another embodiment of the invention, an orthodontic appliance includes a plurality of brackets, an arch wire extending through the brackets, a clamp secured to the arch wire, a hook and a wire having a first end secured to the clamp and a second end secured to the hook. The hook is movable in response to a force applied by an elastic member from a first position in which the hook extends in the labial direction to a second position in which the hook extends in the incisal direction.

In one embodiment, the wire extends in the labial direction. In another embodiment, the wire extends in the distal and mesial directions.

According to yet another embodiment of the invention, an orthodontic appliance includes a plurality of brackets, an arch wire secured to the brackets, a hook and a wire segment. The wire segment is connected to one of the brackets and the hook. The hook is movable in response to a force applied by an elastic member from a first position in which the hook extends in the labial direction to a second position in which the hook extends in the incisal direction. One of the brackets includes a slot and the wire segment extends into the slot.

According to still another embodiment of the present invention, an orthodontic appliance includes a plurality of brackets and at least one tube. An arch wire extends through the brackets and the tube. A hook is pivotally connected to the tube. The hook is secured to the tube by a hinge and is spring loaded. Alternatively, the hook can be held in place magnetically.

Other features of the present invention will become apparent from the following detailed description of the preferred embodiments and accompanying drawings.

BRIEF DESCRIPTION OF THE DRAWINGS

FIG. 15 is a perspective view of an orthodontic appliance according to the present invention utilizing the hook assembly of FIGS. 14a–14d, without an elastic member secured thereto.

FIG. 16 is a perspective view of the orthodontic appliance shown in FIG. 15 with an elastic member secured to the hook assembly.

FIG. 17 is a perspective view of another embodiment of an orthodontic appliance according to the present invention, without an elastic member secured thereto.

FIG. 18 is a perspective view of the orthodontic appliance shown in FIG. 17 with an elastic member secured to the hook assembly.

DETAILED DESCRIPTION OF THE PREFERRED EMBODIMENTS

Figure 1:
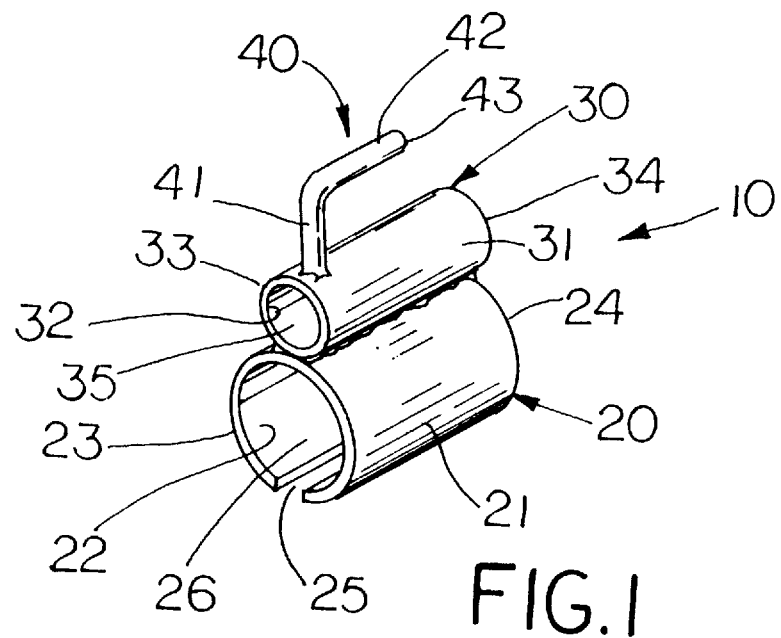
FIG. 1 is a perspective view of an orthodontic hook assembly according to the present invention.

FIG. 1 is a perspective view of a orthodontic hook assembly according to the present invention. Assembly 10 generally includes clamp 20, tube 30 and hook 40. In the embodiment shown, clamp 20 is a generally c-shaped member having an outer surface 21, an inner surface 22, a first end 23 and a second end 24. A slot 25 is cut through outer surface 21 and inner surface 22. A bore 26 extends through clamp 20. Note, however, that clamp 20 does not have to have the shape shown in FIG. 1. Nor does it need to include a slot. Clamp 20 may have various configurations that allow clamp 20 to be secured to the arch wire in either a fixed or pivotable manner, as desired and described below. Various alternative designs of clamps are described below and illustrated in other figures.

Tube 30 includes an outer surface 31, an inner surface 32, a first end 33 and a second end 34. A bore 35 extends through tube 30. Outer surface 31 of tube 30 is joined to outer surface 21 of clamp 20 by welding, although other methods may be used.

Hook 40 includes a first segment 41 extending radially outward from outer surface 31 of tube 30 and a second segment 42 disposed at a generally right angle to first segment 41. Second segment 42 extends in generally the same direction as the axes of bores 26 and 35 and terminates in a free end 43. Hook 40 is secured to outer surface 31 of tube 30 by welding or other means.

Figure 2:
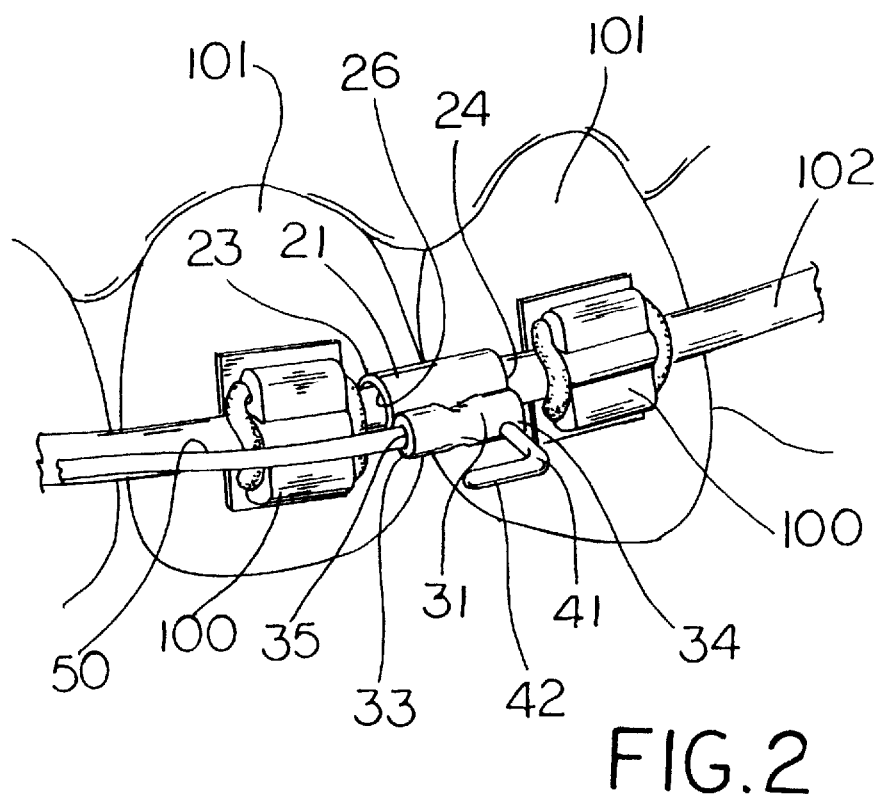
FIG. 2 is a perspective view of an orthodontic appliance according to the present invention utilizing the hook assembly of FIG. 1, without an elastic member secured thereto.

FIG. 2 is a perspective view of an orthodontic appliance according to the present invention utilizing the orthodontic hook assembly shown in FIG. 1. Hook assembly 10 is shown secured to a patient's braces. The braces typically include a plurality of brackets 100 secured to the teeth 101 with an arch wire 102 extending through brackets 100. Arch wire 102 also extends through bore 26 of clamp 20. Clamp 20 is then crimped such that slot 25 is closed. This prevents clamp 20 from disengaging arch wire 102. Note, however, that clamp 20 should not be crimped such that it is fixed in a stationary position on arch wire 102. Rather, clamp 20 must be free to rotate about arch wire 102.

A second wire segment 50 is connected to some of the brackets 100. Wire segment 50 is preferably a shape memory wire made from a nickel-titanium alloy or another resilient wire. One end of wire 50 extends into bore 35 of tube 30. Tube 30 is then crimped such that it is securely fastened to wire segment 50 and does not rotate about wire segment 50. Wire segment 50 is shaped and installed such that it holds hook 40 in the position shown, that is extending in the labial direction, when no elastic member is secured to hook 40.

Figure 3:
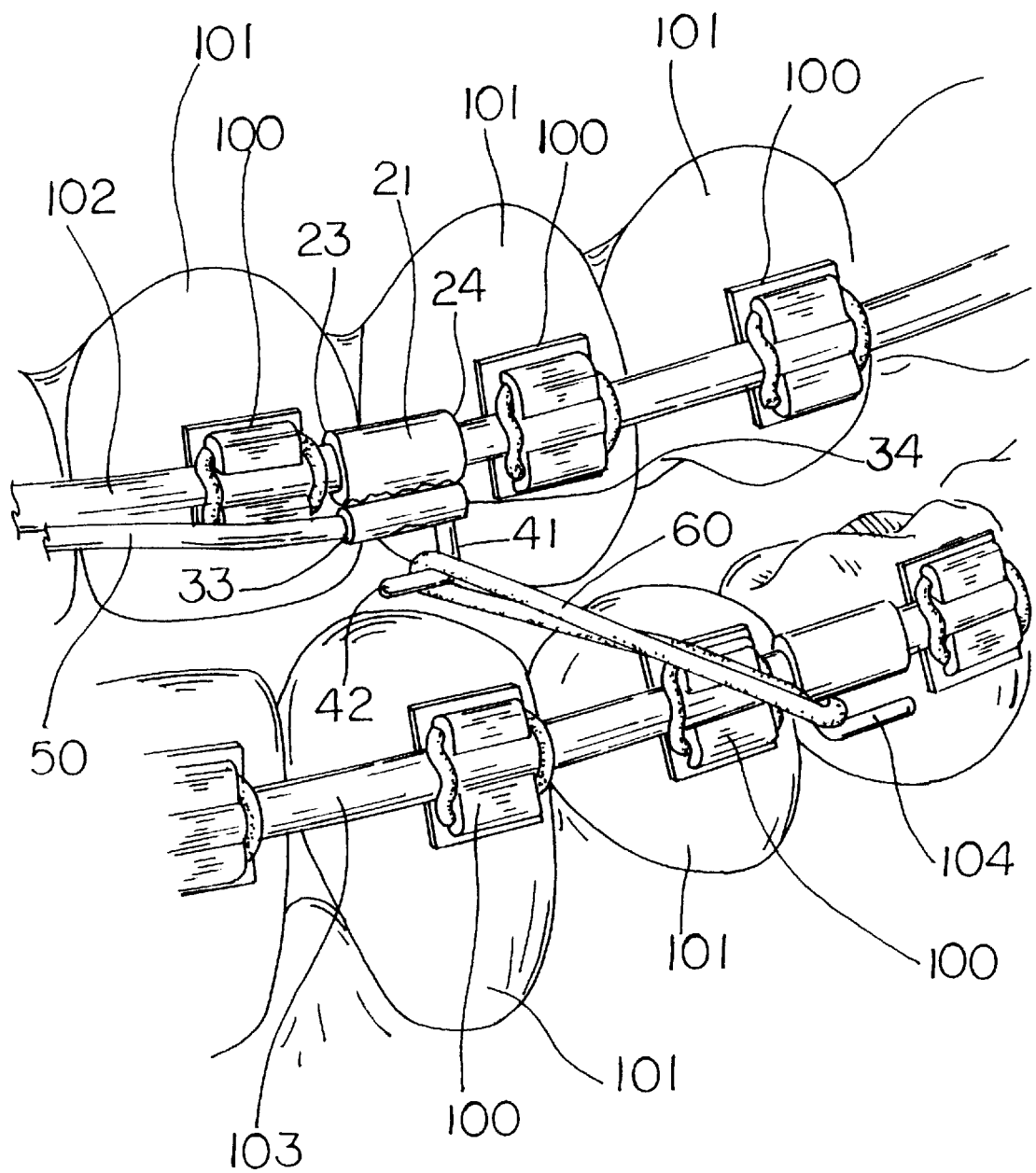
FIG. 3 is a perspective view of the orthodontic appliance shown in FIG. 2 with an elastic member secured to the hook assembly.

When an elastic member 60 is secured about hook 40 and stationary hook 104 secured to lower arch wire 103, as shown in FIG. 3, or, alternatively, to a stationary hook on a molar tube, the force applied by elastic member 60 causes clamp 20 to pivot about arch wire 102 such that hook 40 extends downwardly in the incisal direction. When elastic member 60 is removed, wire segment 50 will return to its original position, thus causing clamp 20 to pivot about arch wire 102 and return hook 40 to its original position extending in the labial direction. In this manner, if the patient does not wear his or her elastics, hook 40 will protrude in the labial direction and poke the inside of the patient's mouth. This causes discomfort and encourages the patient to apply the elastics such that hook 40 pivots to the incisal direction and is no longer irritating the inside of the mouth.

Figure 4:
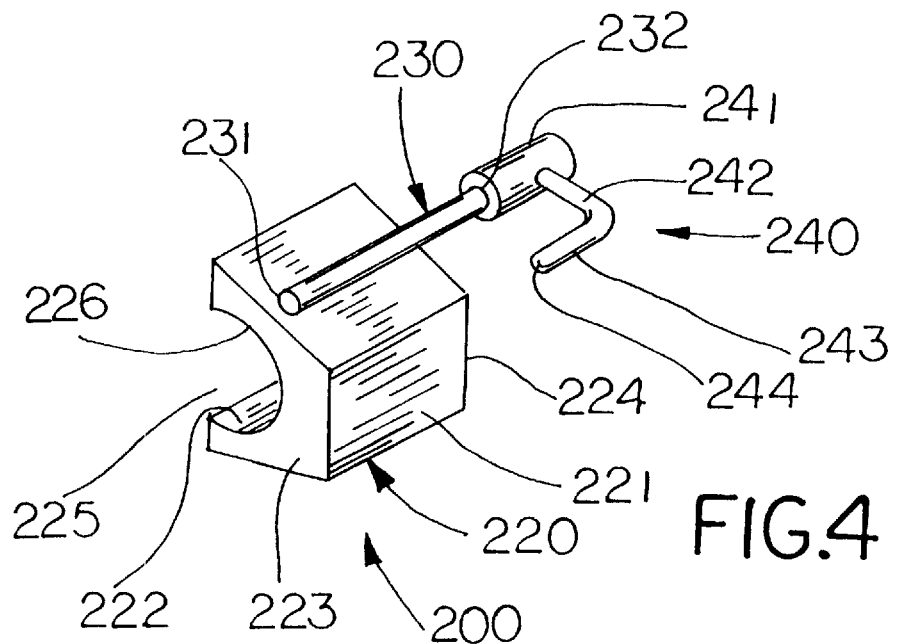
FIG. 4 is a perspective view of another embodiment of an orthodontic hook assembly according to the present invention.

FIG. 4 shows another embodiment of an orthodontic hook assembly according to the present invention. Hook assembly 200 generally includes a clamp 220, wire 230 and hook 240. In the embodiment shown, clamp 220 has an outer surface 221, an inner surface 222, a first end 223 and a second end 224. Clamp 220 is generally c-shaped and includes a slot 225 cut through outer surface 221 and inner surface 222. A bore 226 extends through clamp 220. Again, the clamp can be any one of a number of configurations. For example, slot 225 can be eliminated.

Wire 230 is a resilient wire, preferably made from a shape memory nickel-titanium alloy. Wire 230 includes a first end 231 and a second end 232. Wire 230 is secured to the exterior surface 221 of clamp 220 by welding or other means. Wire 230 extends in generally the same direction as the axis of bore 226.

Hook 240 includes a first segment 241 generally coaxial with wire 230 and secured to second end 232 thereof. A second segment 242 of hook 240 extends from first segment 241 at a generally right angle thereto. Third segment 243 of hook 240 extends from the opposite end of second segment 242 at a generally right angle thereto, generally parallel to wire 230, and terminates in free end 244.

Figure 5:
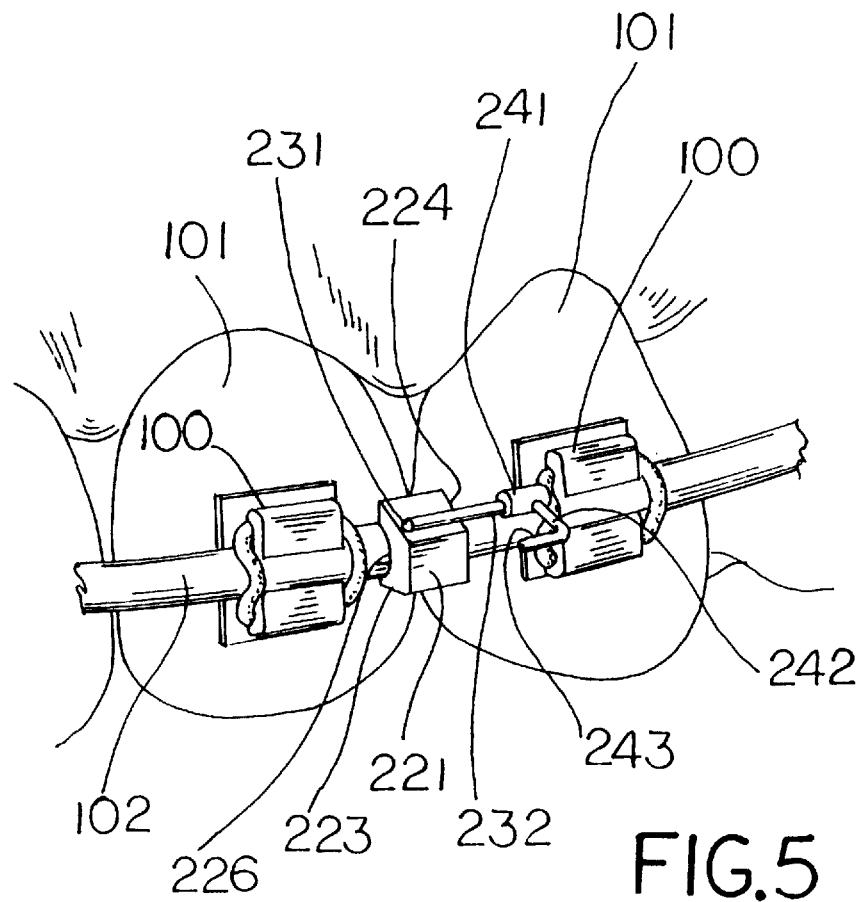
FIG. 5 is a perspective view of an orthodontic appliance according to the present invention utilizing the hook assembly of FIG. 4, without an elastic member secured thereto.
Figure 6:
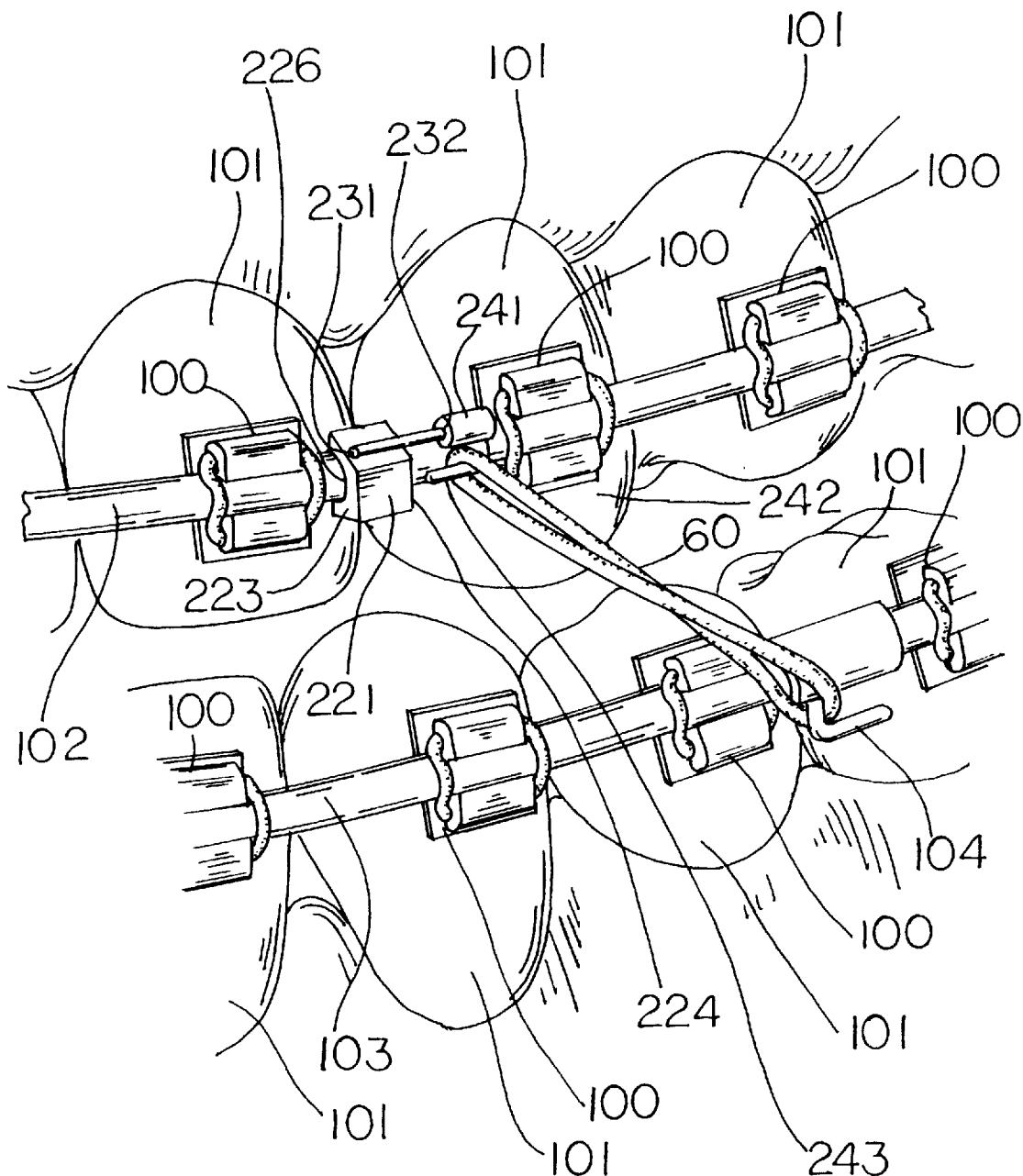
FIG. 6 is a perspective view of the orthodontic appliance shown in FIG. 5 with an elastic member secured to the hook assembly.

FIG. 5 shows the hook assembly of FIG. 4 secured to orthodontic braces without an elastic member applied to hook 240. In this embodiment, clamp 220 is crimped about arch wire 102 such that it cannot rotate with respect to arch wire 102. In this position, hook 240 extends outwardly in the labial direction. When an elastic member 60 is applied to hook 240 (FIG. 6), the resulting force bends wire 230 downwardly such that hook 240 extends in the incisal direction. When elastic member 60 is removed, wire 230 springs back to its original position and hook 240 extends once again in the labial direction.

Figure 7:
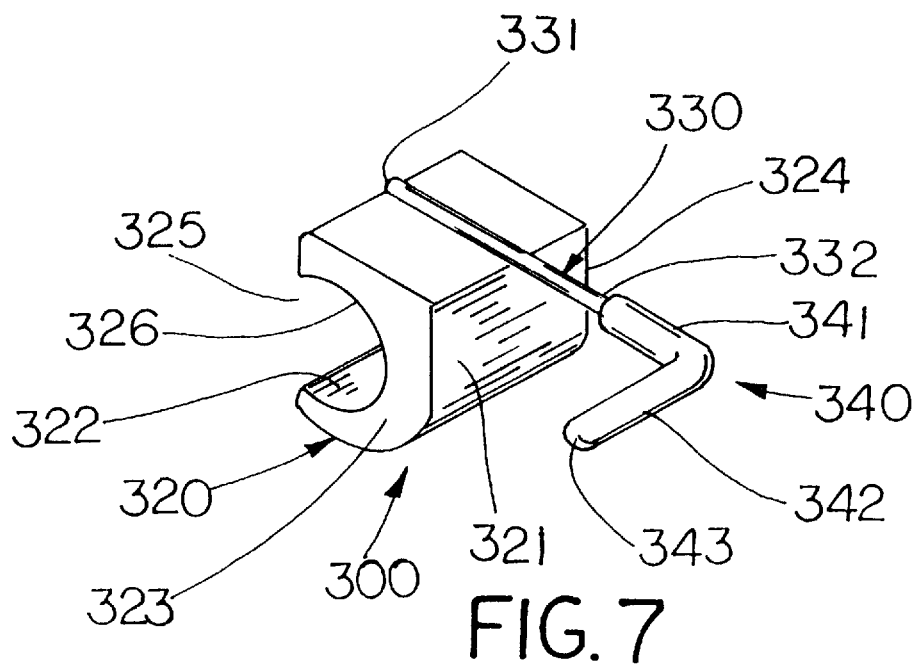
FIG. 7 is a perspective view of another embodiment of an orthodontic hook assembly according to the present invention.

FIG. 7 shows another embodiment of an orthodontic hook assembly according to the present invention. Hook assembly 300 generally includes a clamp 320, wire 330 and hook 340. In the embodiment shown, clamp 320 has an outer surface 321, an inner surface 322, a first end 323 and a second end 324. Clamp 320 is generally c-shaped and includes a slot 325 cut through outer surface 321 and inner surface 322. A bore 326 extends through clamp 320.

Wire 330 is a resilient wire, preferably made from a nickel-titanium shape memory alloy. Wire 330 includes a first end 331 and a second end 332. Wire 330 is secured to the exterior surface 321 of clamp 320 by welding or other means. Wire 330 extends generally perpendicularly to the longitudinal axis of bore 326.

Hook 340 includes a first segment 341 generally coaxial with wire 330 and secured to second end 332 thereof. A second segment 342 of hook 340 extends from first segment 341 at a generally right angle thereto and terminates in a free end 343.

Figure 8:
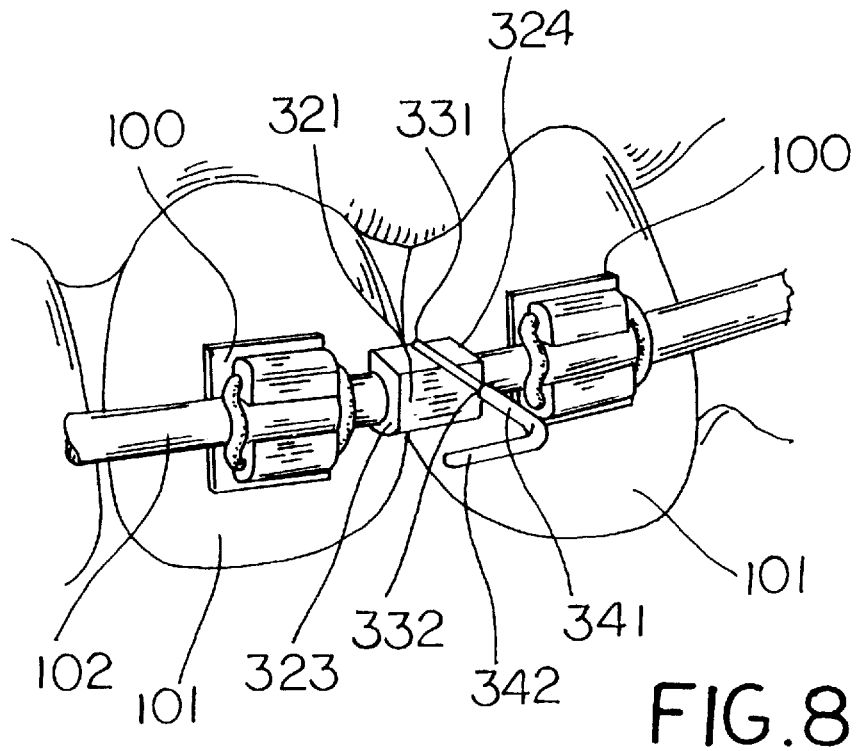
FIG. 8 is a perspective view of an orthodontic appliance according to the present invention utilizing the hook assembly of FIG. 7, without an elastic member secured thereto.
Figure 9:
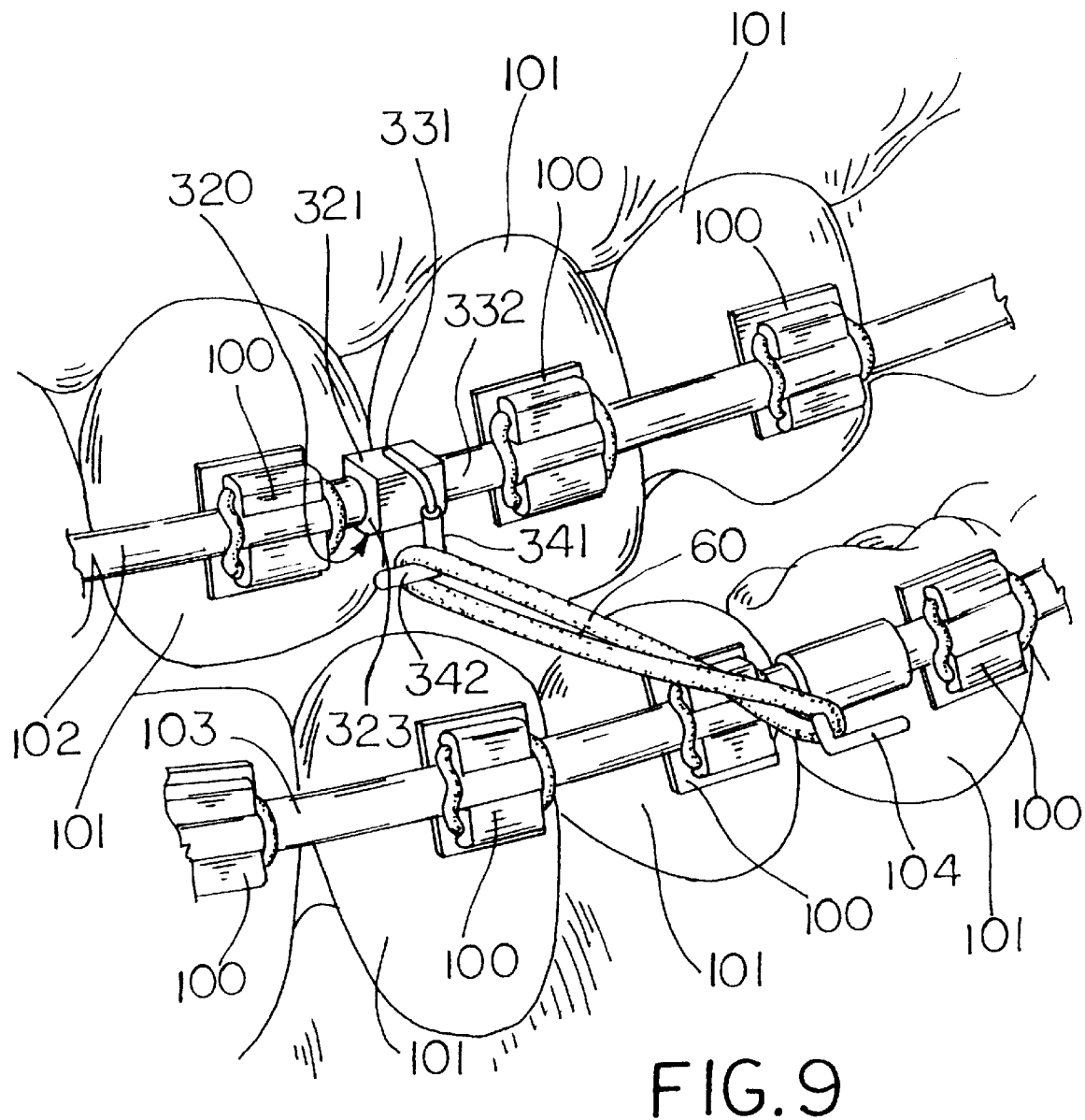
FIG. 9 is a perspective view of the orthodontic appliance shown in FIG. 8 with an elastic member secured to the hook assembly.

FIG. 8 shows the hook assembly of FIG. 7 secured to orthodontic braces without an elastic member applied to hook 340. In this embodiment, clamp 320 is crimped about arch wire 102 such that it cannot rotate with respect to arch wire 102. In this position, hook 340 extends outwardly in a labial direction. When an elastic member 60 is applied to hook 340 (FIG. 9), the resulting force bends wire 330 downwardly such that hook 340 extends in the incisal direction. When elastic member 60 is removed, wire 330 springs back to its original position and hook 340 extends once again in the labial direction.

Figure 10:
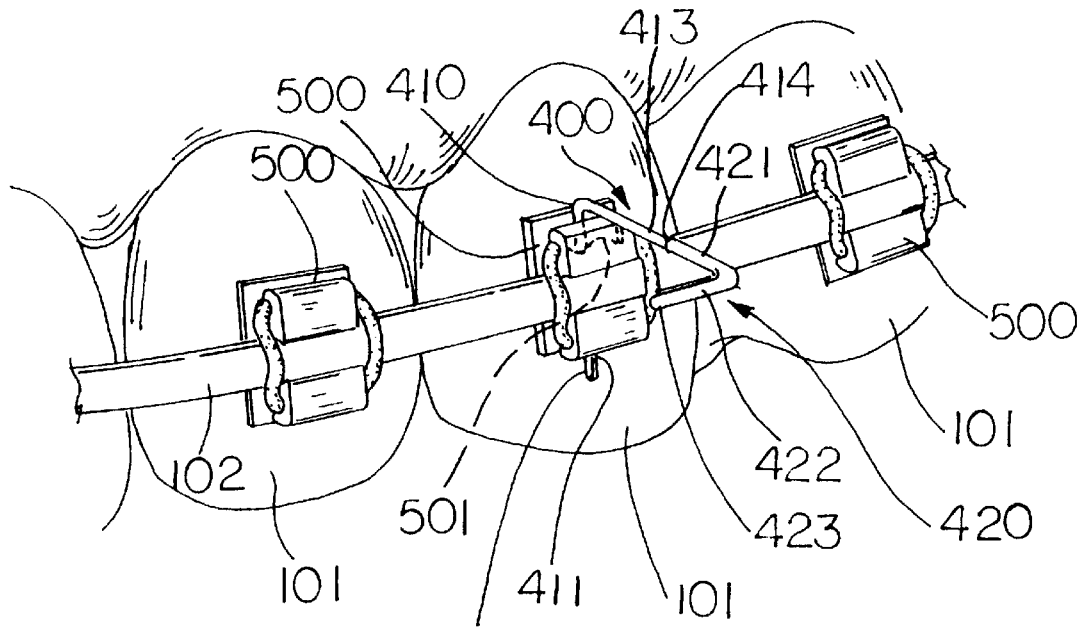
FIG. 10 is a perspective view of another embodiment of an orthodontic appliance according to the present invention, without an elastic member secured thereto.

FIG. 10 shows yet another embodiment of an orthodontic hook assembly according to the present invention. In this embodiment, hook assembly 400 generally includes a wire 410 and a hook 420. Wire 410 includes a first segment 411 having a free end 412 and a second en that transitions into a second segment 413 disposed at a generally right angle to first segment 411. Second segment 413 terminates in a second end 414. Wire 410 is preferably made from a resilient material or a nickel-titanium shape memory alloy.

Hook 420 includes a first segment 421 extending generally coaxial with second segment 413 of wire 410 and a second segment 422 extending at a generally right angle to first segment 421. Second segment 422 terminates in a free end 423.

Figure 11:
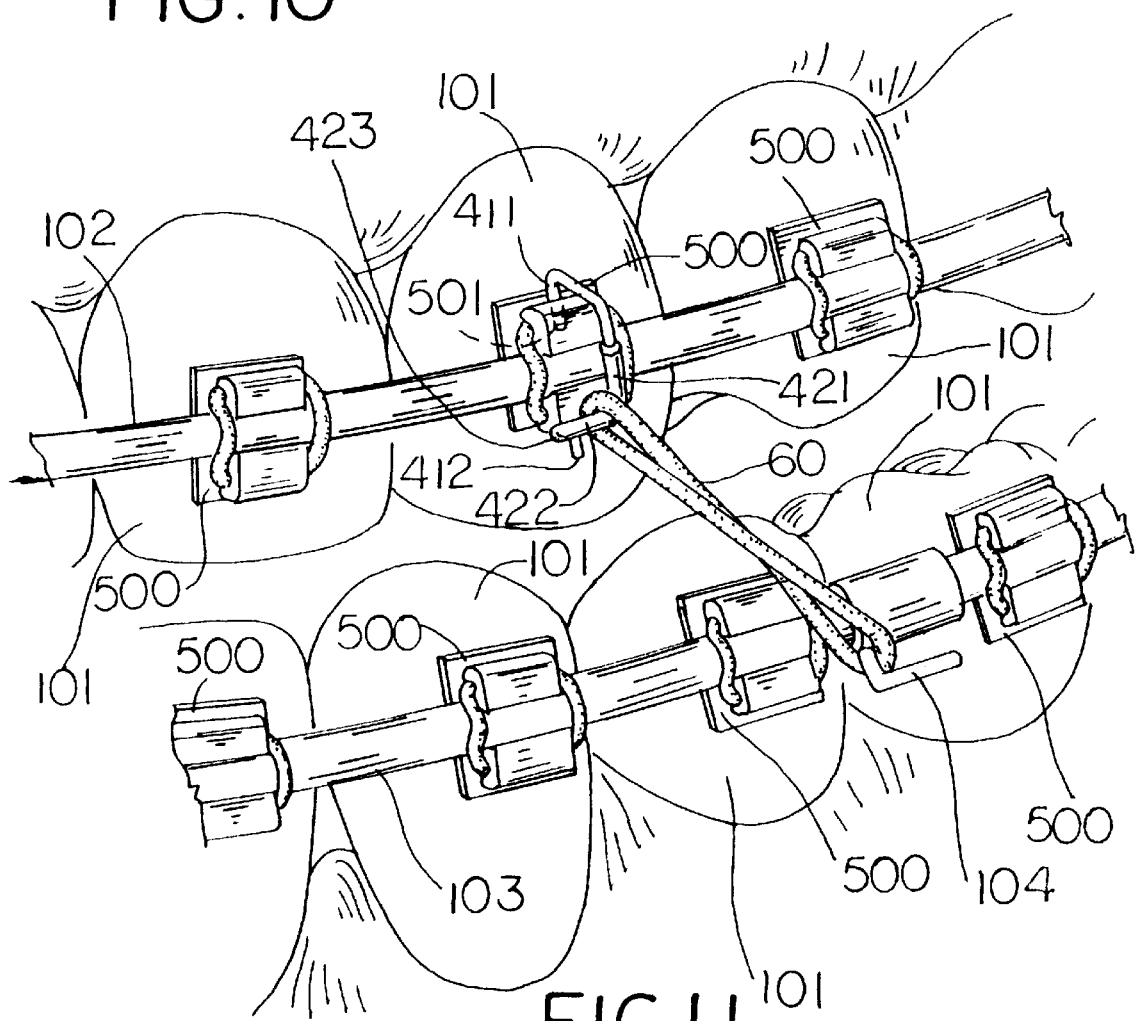
FIG. 11 is a perspective view of the orthodontic appliance shown in FIG. 10 with an elastic member secured to the hook assembly.

In use, first end 412 of first segment 411 is inserted through a slot 501 in a bracket 500 and secured therein. In this manner, hook 420 extends in the labial direction and contacts the interior of the patient's mouth when an elastic member is not applied to hook 420. When an elastic member 60 is applied (FIG. 11), wire 410 bends as shown and hook 420 extends in the incisal direction so as not to irritate the interior of the patient's mouth. Again, when elastic member 60 is removed, wire 410 returns to its original position such that hook 420 extends in the labial direction.

Figure 12:
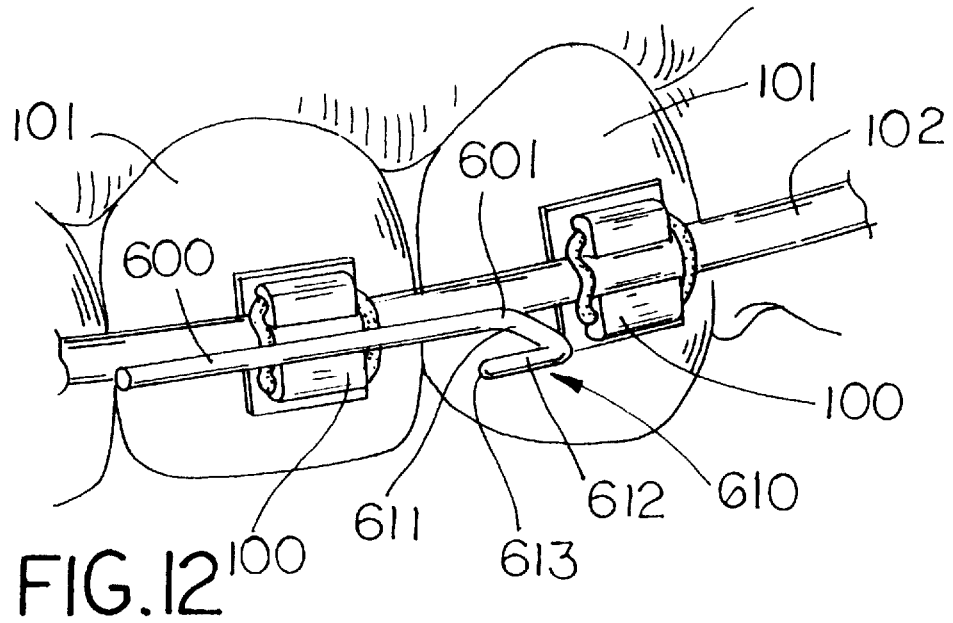
FIG. 12 is a perspective view of another embodiment of an orthodontic appliance according to the present invention, without an elastic member secured thereto.

FIG. 12 shows yet another embodiment of the present invention. In this embodiment, a second wire 600 is positioned over arch wire 102 and secured to brackets 100 by ligature ties. Each end of second wire 600 terminates in a hook 610. Hook 610 includes a first segment 611 that extends generally perpendicular to end 601 of wire 600. Hook 610 further includes a second segment 612 disposed generally perpendicular to first segment 611. Second segment 612 terminates in a free end 613.

Figure 13:
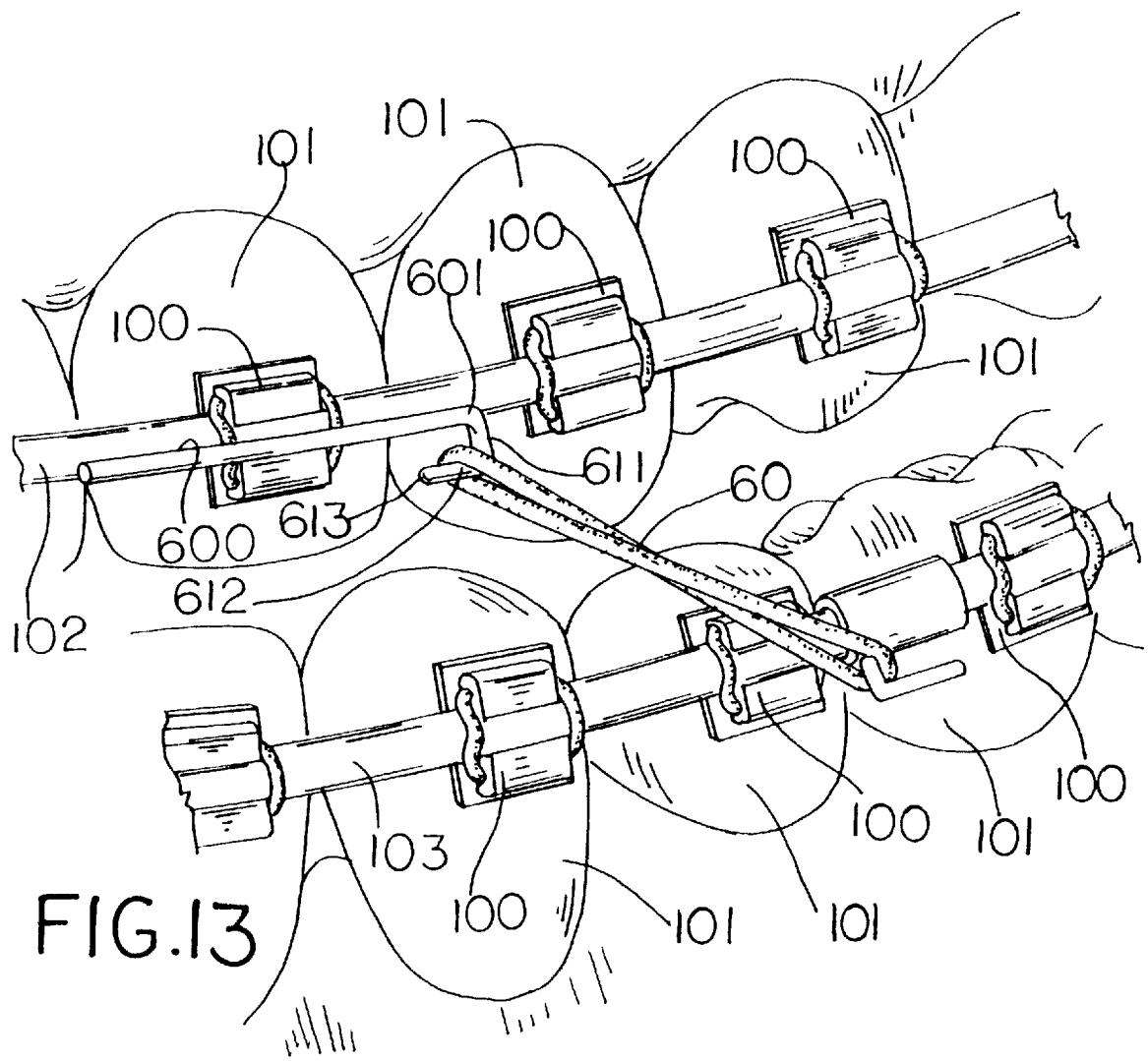
FIG. 13 is a perspective view of the orthodontic appliance shown in FIG. 12 with an elastic member secured to the hook assembly.

As can be seen in FIG. 13, when elastic member 60 is placed around hook 610 and stationary hook 104, hook 610 bends downward in the incisal direction. In this manner, as with the other embodiments, hook 610 will not poke the inside of the patient's mouth as long as the elastics are in place.

Figure 14A:
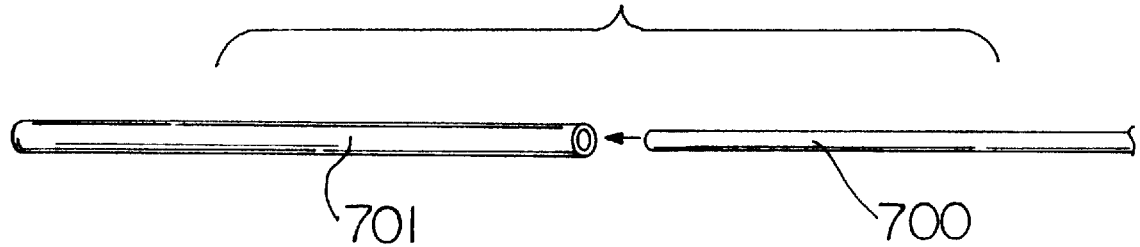
FIGS. 14a–14d illustrate another embodiment of an orthodontic hook assembly according to the present invention.
Figure 14B:
Figure 14C:
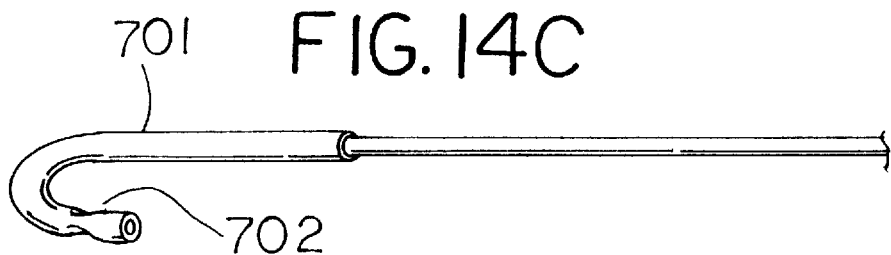
Figure 14D:
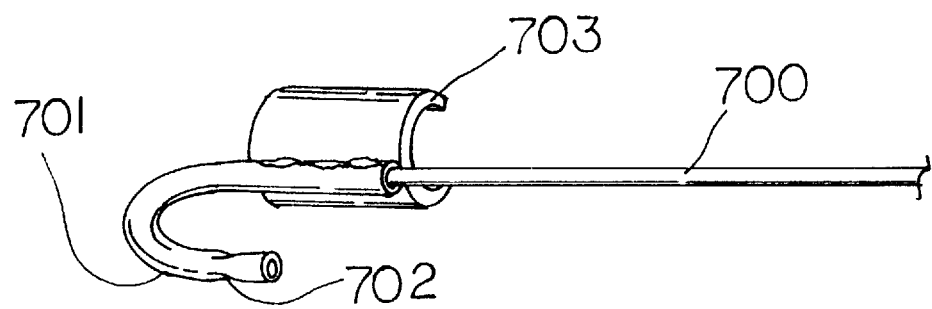

FIGS. 14a–14d show yet another embodiment of an orthodontic hook assembly according to the present invention. In this embodiment, a shape memory wire 700 is inserted into a tube 701. Tube 701 is then crimped as shown at 702 to secure tube 701 to wire 700. Wire 700 and tube 701 are then bent in the form of a hook as shown in FIG. 14c. Tube 701 is then secured to a clamp 703 as shown in FIG. 14d. To install the hook assembly shown in FIGS. 14a–14d, clamp 703 is placed about arch wire 102 so that it is free to rotate as described above in conjunction with the embodiment of FIG. 1. Wire 700 extends through the brackets of the braces. In this manner, the hook assembly will pivot between a position in which it pokes the inside of the mouth (FIG. 15) and one in which it does not (FIG. 16) depending upon whether or not the patient is wearing his or her elastics.

FIGS. 17 and 18 show still another embodiment of an orthodontic hook assembly according to the present invention. In this embodiment, a magnet 800 is positioned on arch wire 102 and is free to rotate thereabout. A hook 802 extends from magnet 800. A second magnet 801 is positioned on arch wire 102 adjacent first magnet 800 and is fixed so that it cannot rotate. The magnets are aligned such that the north pole of one magnet is adjacent the south pole of the other magnet. In this manner, the magnetic forces of attraction between magnets 800 and 801 hold hook 802 in the position shown in FIG. 17. When elastic member 60 is applied to hook 802 (FIG. 18), the force of the elastic member overcomes the magnetic force and causes magnet 800 to rotate as shown such that hook 802 is no longer irritating the inside of the patient's mouth. When elastic member 60 is removed, the magnetic force will restore hook 802 to the position shown in FIG. 17.

Figure 19:
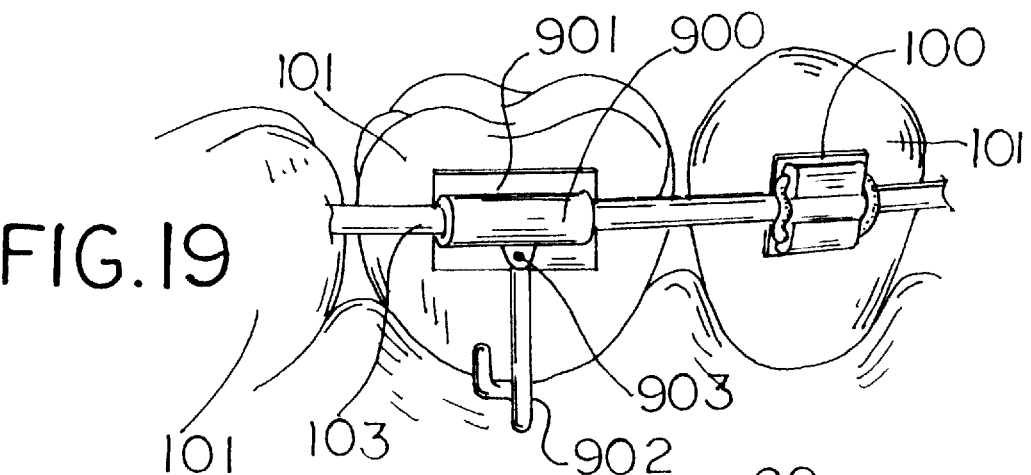
FIG. 19 is a perspective view of another embodiment of an orthodontic appliance according to the present invention, without an elastic member secured thereto.
Figure 20:
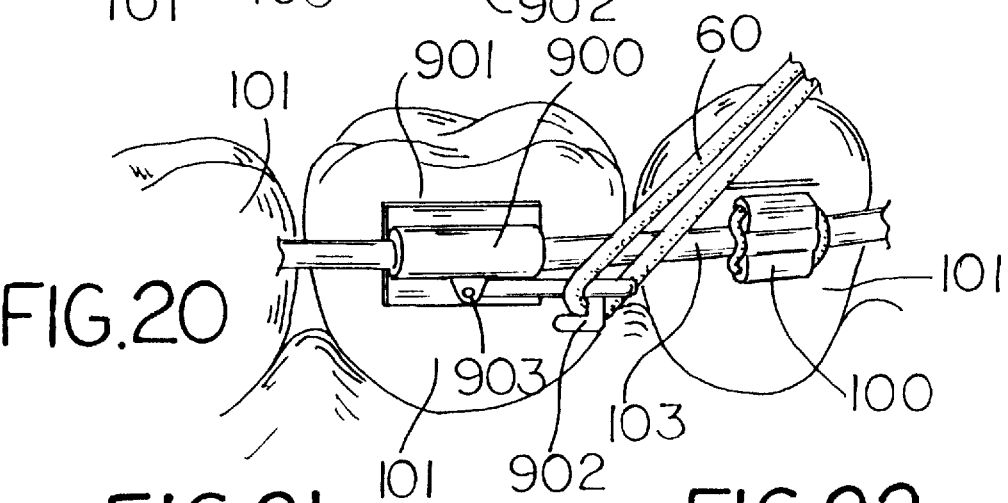
FIG. 20 is a perspective view of the orthodontic appliance shown in FIG. 19 with an elastic member secured to the hook assembly.

FIGS. 19 and 20 show yet another embodiment of the present invention. In this embodiment, arch wire 103 passes through a molar tube 900 secured to a base 901. Base 901 is secured to tooth 101. A hook 902 extends in the gingival direction from tube 900. Hook 902 is pivotally secured to tube 900 as by a hinge 903. The hook 902 is spring loaded such that it extends as shown in FIG. 19 when elastic member 60 is not secured to hook 902. Alternatively, hook 902 may be held in the position shown by magnetic force. When elastic member 60 is applied to hook 902 (FIG. 20), hook 902 pivots as shown so as not to irritate the interior of the patient's mouth. In this embodiment, the opposite end of elastic member 60 is secured to a stationary hook positioned on the upper molars.

Figure 21:
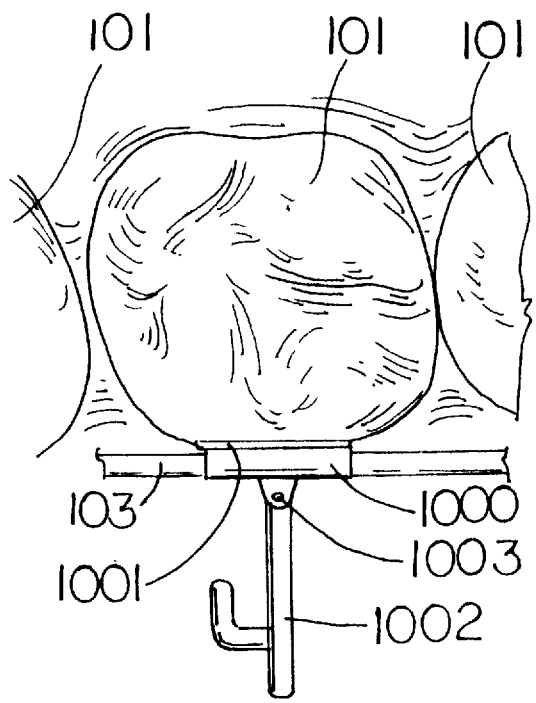
FIG. 21 is a perspective view of another embodiment of an orthodontic appliance according to the present invention, without an elastic member secured thereto.
Figure 22:
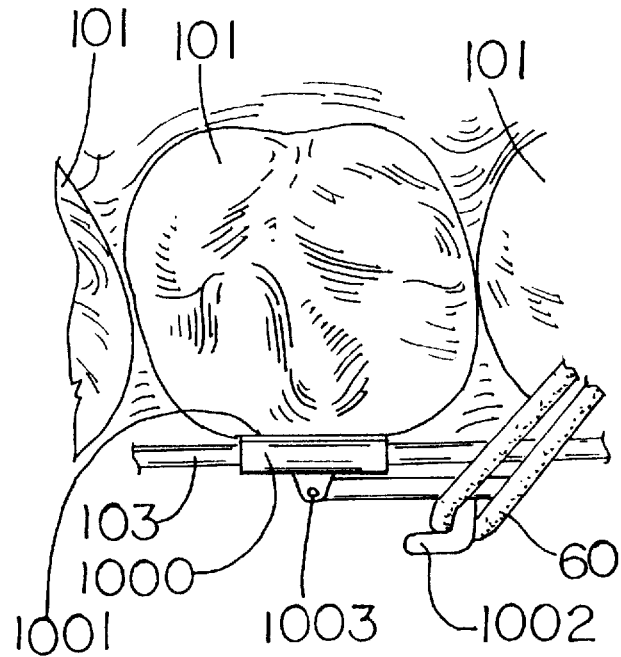
FIG. 22 is a perspective view of the orthodontic appliance shown in FIG. 21 with an elastic member secured to the hook assembly.

FIGS. 21 and 22 show an occlusal view of yet another embodiment of the present invention. In this embodiment, arch wire 103 extends through a molar tube 1000 secured to a base 1001. Base 1001 is secured to tooth 100 such that hook 1002 extends in the labial direction. Hook 1002 is spring loaded and is pivotally secured to tube 1000 by a hinge 1003. Without an elastic on hook 1002, the hook pokes the inside of the patient's mouth. When elastic member 60 is secured to hook 1002, it pivots as shown in FIG. 22.

Although the invention has been described and illustrated in detail, it is to be clearly understood that the same is by way of illustration and example only and is not to be taken by way of limitation. Numerous changes can be made to the embodiments shown without departing from the scope of the invention. For example, the clamps, hooks and other components illustrated can be of shapes other than those shown. Also, more than one movable hook assembly may be employed. For example, two such assemblies, one on each side of the patient's mouth, may be used. Accordingly, the spirit and scope of the invention are to be limited only by the terms of the appended claims.

What is claimed is:

1. An orthodontic appliance, comprising:
    a plurality of brackets;
    an arch wire connected to the plurality of brackets; and
    a hook for receiving the elastic member, the hook being movable from a first position wherein the hook extends in the labial or buccal direction when the elastic member is not positioned about the hook to a second position wherein the hook extends in the occlusal or incisal direction when the elastic member is positioned about the hook.

2. The orthodontic appliance according to claim 1, further comprising a clamp pivotable about the arch wire, a tube connected to the clamp and to the hook, and a second wire connected to the tube.

3. The orthodontic appliance according to claim 1, further comprising a second wire secured to the hook.

4. The orthodontic appliance according to claim 3, wherein the second wire is a shape memory wire.

5. The orthodontic appliance according to claim 3, further comprising a tube connected to the hook and wherein the second wire extends into the tube.

6. The orthodontic appliance according to claim 5, wherein the second wire is connected to the tube.

7. The orthodontic appliance according to claim 3, wherein the second wire is connected to at least one of the brackets.

8. The orthodontic appliance according to claim 3, wherein the second wire is resilient.

9. The orthodontic appliance according to claim 1, further comprising a clamp connected to the hook and wherein the arch wire extends into the clamp.

10. The orthodontic appliance according to claim 9, wherein the clamp is pivotable about the arch wire.

11. The orthodontic appliance according to claim 1 further comprising a clamp pivotable about the arch wire, a tube connected to the clamp and a second wire extending into the tube.

12. The orthodontic appliance according to claim 11 wherein the tube and second wire are bent to form the hook.

13. The orthodontic appliance according to claim 1 further comprising a first magnet secured to the hook and a second magnet secured to the arch wire.

14. The orthodontic appliance according to claim 13 wherein the arch wire extends through the first magnet.

15. The orthodontic appliance according to claim 13 wherein the first magnet is pivotable about the arch wire.

16. An orthodontic appliance, comprising:
    a plurality of brackets;
    an arch wire extending through the brackets;
    a clamp secured to the arch wire;
    a hook; and
    a wire segment having a first end secured to the clamp and a second end secured to the hook, wherein the hook is movable in response to a force applied by an elastic member from a first position in which the hook extends in the labial direction to a second position in which the hook extends in the incisal direction.

17. The orthodontic appliance according to claim 16, wherein the wire segment extends in the labial direction.

18. The orthodontic appliance according to claim 16, wherein the wire segment extends in the distal and mesial directions.

19. The orthodontic appliance according to claim 16, wherein the wire segment is resilient.

20. The orthodontic appliance according to claim 16, wherein the clamp comprises a generally c-shaped member.

21. The orthodontic appliance according to claim 16, wherein the clamp is crimped about the arch wire.

22. An orthodontic appliance, comprising:
    a plurality of brackets;
    an arch wire secured to the brackets;
    a hook;
    a wire segment connected to one of the brackets and the hook; and
    wherein the hook is movable in response to a force applied by an elastic member from a first position in which the hook extends in the labial direction to a second position in which the hook extends in the incisal direction.

23. The orthodontic appliance according to claim 22, further comprising a slot in one of the brackets and wherein the wire segment extends into the slot.

24. The orthodontic appliance according to claim 22, wherein the wire segment includes a first portion extending in the gingival-incisal direction.

25. The orthodontic appliance according to claim 22, wherein the wire segment is resilient.

26. An orthodontic appliance comprising:
    a plurality of brackets;
    at least one tube;
    an arch wire extending through the brackets and the tube; and
    a hook pivotally connected to the tube.

27. The orthodontic appliance according to claim 26 wherein the hook is secured to the tube by a hinge.

28. The orthodontic appliance according to claim 26 wherein the hook is spring loaded.

29. The orthodontic appliance according to claim 26 wherein the hook is held in position by a magnet when there is no elastic member applied to the hook.

30. An orthodontic appliance, comprising:
    a plurality of brackets;
    an arch wire connected to the plurality of brackets;
    a clamp pivotable about the arch wire;
    a hook for receiving an elastic member, the hook being movable from a first position when the elastic member is not positioned about the hook to a second position when the elastic member is positioned about the hook;
    a tube connected to the clamp and to the hook; and
    a second wire connected to the tube.

31. The orthodontic appliance according to claim 30, wherein the hook extends in the labial or buccal direction when the elastic member is not positioned about the hook.

32. The orthodontic appliance according to claim 30, wherein the hook extends in the incisal direction when the elastic member is positioned about the hook.

33. The orthodontic appliance according to claim 30, wherein the second wire is a shape memory wire.

34. The orthodontic appliance according to claim 30, further comprising a tube connected to the hook and wherein the second wire extends into the tube.

35. The orthodontic appliance according to claim 30, wherein the second wire is connected to at least one of the brackets.

36. The orthodontic appliance according to claim 30, wherein the second wire is resilient.

37. An orthodontic appliance, comprising:

a plurality of brackets;

an arch wire connected to the plurality of brackets;

a hook for receiving an elastic member, the hook being movable from a first position when the elastic member is not positioned about the hook to a second position when the elastic member is positioned about the hook; and a second wire secured to the hook.

38. The orthodontic appliance according to claim 37 wherein the second wire is a shape memory wire.

39. The orthodontic appliance according to claim 37, further comprising a tube connected to the hook and wherein the second wire extends into the tube.

40. The orthodontic appliance according to claim 37, wherein the second wire is connected to the tube.

41. The orthodontic appliance according to claim 37, wherein the second wire is connected to at least one of the brackets.

42. The orthodontic appliance according to claim 37, wherein the second wire is resilient.

43. The orthodontic appliance according to claim 37, further comprising a clamp pivotable about the arch wire, a tube connected to the clamp and to the hook, and wherein the second wire is connected to the tube.

44. The orthodontic appliance according to claim 37, wherein the hook extends in the labial or buccal direction when the elastic member is not positioned about the hook.

45. The orthodontic appliance according to claim 37, wherein the hook extends in the incisal direction when the elastic member is positioned about the hook.

46. The orthodontic appliance according to claim 37, further comprising a clamp connected to the hook and wherein the arch wire extends into the clamp.

47. The orthodontic appliance according to claim 46, wherein the clamp is pivotable about the arch wire.

48. The orthodontic appliance according to claim 37 further comprising a clamp pivotable about the arch wire, a tube connected to the clamp and wherein the second wire extends into the tube.

49. An orthodontic appliance, comprising:

a plurality of brackets;

an arch wire connected to the plurality of brackets;

a clamp pivotable about the arch wire;

a tube connected to the clamp;

a second wire extending into the tube; and a hook for receiving an elastic member, the hook being movable from a first position when the elastic member is not positioned about the hook to a second position when the elastic member is positioned about the hook.

50. The orthodontic appliance according to claim 49 wherein the tube and second wire are bent to form the hook.

51. The orthodontic appliance according to claim 49, wherein the tube is connected to the hook.

52. The orthodontic appliance according to claim 49, wherein the hook extends in the labial or buccal direction when the elastic member is not positioned about the hook.

53. The orthodontic appliance according to claim 49, wherein the hook extends in the incisal direction when the elastic member is positioned about the hook.

54. The orthodontic appliance according to claim 49, wherein the second wire is a shape memory wire.

55. The orthodontic appliance according to claim 49, wherein the second wire is connected to at least one of the brackets.

56. The orthodontic appliance according to claim 49, wherein the second wire is resilient.

57. An orthodontic appliance, comprising:

a plurality of brackets;

an arch wire connected to the plurality of brackets;

a hook for receiving an elastic member, the hook being movable from a first position when the elastic member is not positioned about the hook to a second position when the elastic member is positioned about the hook;

a first magnet secured to the hook; and a second magnet secured to the arch wire.

58. The orthodontic appliance according to claim 57 wherein the arch wire extends through the first magnet.

59. The orthodontic appliance according to claim 57 wherein the first magnet is pivotable about the arch wire.

60. The orthodontic appliance according to claim 57, wherein the hook extends in the labial or buccal direction when the elastic member is not positioned about the hook.

61. The orthodontic appliance according to claim 57, wherein the hook extends in the incisal direction when the elastic member is positioned about the hook.

* * * * *

UNITED STATES PATENT AND TRADEMARK OFFICE
CERTIFICATE OF CORRECTION

PATENT NO. : 5,873,716
DATED : February 23, 1999
INVENTOR(S) : Christopher K. Kesling Page 1 of 1

It is certified that error appears in the above-identified patent and that said Letters Patent is hereby corrected as shown below:

<u>Column 7:</u>
Claim 1, between lines 1 and 2, insert a line reciting --an elastic member;--.

Signed and Sealed this

Twelfth Day of June, 2001

*Attest:*

*Attesting Officer*

NICHOLAS P. GODICI
*Acting Director of the United States Patent and Trademark Office*